United States Patent [19]

Porteous

[11] Patent Number: 5,009,056
[45] Date of Patent: * Apr. 23, 1991

[54] METHOD FOR PREPARING FINGER MOUNTABLE DISPENSING CUPS

[76] Inventor: Don D. Porteous, 2794 Moraga Dr., Los Angeles, Calif. 90024

[*] Notice: The portion of the term of this patent subsequent to Jul. 4, 2006 has been disclaimed.

[21] Appl. No.: 457,889

[22] Filed: Dec. 27, 1989

Related U.S. Application Data

[63] Continuation-in-part of Ser. No. 278,570, Dec. 1, 1988, abandoned, which is a continuation-in-part of Ser. No. 140,303, Dec. 31, 1987, Pat. No. 4,844,308, which is a continuation-in-part of Ser. No. 4,543, Jan. 16, 1987, Pat. No. 4,717,057.

[51] Int. Cl.$^5$ .................... B65B 47/02; B65B 61/14; B65B 61/18
[52] U.S. Cl. ........................ 53/412; 43/413; 43/453
[58] Field of Search ............... 53/134, 373, 412, 413, 53/420, 453, 471, 477, 478, 485, 454, 559, 560; 206/63.5, 633; 224/217; 433/49, 97, 163

[56] References Cited

U.S. PATENT DOCUMENTS

| | | | |
|---|---|---|---|
| 2,970,379 | 2/1961 | Hardgrove | 63/15 |
| 3,660,960 | 5/1972 | Inman | 53/471 X |
| 4,372,098 | 2/1983 | Mason | 53/412 |
| 4,571,924 | 2/1986 | Bahrani | 53/453 |
| 4,717,057 | 1/1988 | Porteous | 433/97 X |
| 4,844,308 | 7/1989 | Porteous | 224/217 |
| 4,871,555 | 10/1989 | Schwartz et al. | 53/413 X |

Primary Examiner—Robert L. Spruill
Assistant Examiner—Linda B. Johnson
Attorney, Agent, or Firm—Donald Diamond

[57] ABSTRACT

A sealed dispensing cup is prepared by forming a portion of a plastic sheet into a cup, adding dispensable material to the cup, placing a sealable closure over the open end of the cup and marginally beyond the periphery of the open end to provide an overlap area that includes a lateral rim section, sealing the closure to the lateral rim section, excising the lateral rim section, with its subtending cup, from the plastic sheet in a configuration that includes an elongated handle portion extending outwardly from the rim, and shaping the elongated handle portion into the form of a finger mount.

8 Claims, 4 Drawing Sheets

METHOD FOR PREPARING FINGER MOUNTABLE DISPENSING CUPS

CROSS-REFERENCE TO RELATED APPLICATION

This application is a continuation-in-part of U.S. patent application No. 278,570, filed Dec. 1, 1988, now abandoned, entitled Method For Preparing Finger Mountable Dispensing Cups, which is a continuation-in-part of U.S. patent application No. 140,303, filed Dec. 31, 1987 and entitled Dental Dispensing Cup With Integrated Finger Mount, now U.S. Pat. No. 4,844,308 dated July 4, 1989, which is a continuation-in-part of U.S. patent application No. 004,543, filed Jan. 16, 1987 and entitled Dental Paste Cup with Integrated Finger Mount, now U.S. Pat. No. 4,717,057 dated Jan. 5, 1988.

BACKGROUND OF THE INVENTION

1. Field of the Invention

This invention relates to finger mountable dispensing cups and, more particularly, to a method for preparing disposable, filled and sealed, finger mountable, dispensing cups for use in dental practice.

2. Prior Art

In one packaging format, dental polishing paste adapted for use in dental practice has been supplied to the dental profession in disposable cups, sized for individual patient usage. In this format, the dental paste cup generally comprises a cylindrical container having an open mouth which is continuous with an outwardly disposed lateral flange. A closure in the form of a thin cover sheet overlies the mouth of the container and is secured to the upper surface of the lateral flange. The closure includes a laterally extending, pull-open tab to facilitate complete removal of the closure at the time of use and thereby permit unimpeded access to the dental paste in the container.

The aforesaid dental paste cup is adapted to be used with a sterilizable and reusable, metallic finger-mountable holder. In an illustrative prior art embodiment, the holder, which is constructed from thin sheet metal, generally comprises a cylindrical member that is continuous with an upwardly, outwardly, and downwardly extending, finger-mountable member having its terminus in substantial spaced relationship to the cylindrical member. The finger-mountable member, in this embodiment, has an inverted U-shaped or horseshoe-like configuration. In use, the body of the dental paste cup is passed through the cylindrical member so as to engage the top of this member with the underside of the cup's lateral flange. The U-shaped finger mount is then passed over the finger which provides a support for the holder-cup combination. Thereafter, the clinician removes the closure from the dental paste cup and dips the tip of a power actuated applicator into the cup to thereby obtain a suitable quantity of dental paste for use in polishing a patient's teeth. A significant problem associated with the repeated use of dental cup holders incorporating U-shaped finger grips is that such holders tend to slip and slide about the finger upon application of a dipping force to the contents of the dental cup.

Other packaging formats for dental material cups are illustrated by the following patents:

U.S. Pat. No. 3,327,391 (Malm, 1967) discloses a disposable, clear acetate, dental material cup containing dental medicaments or pumices and provided with a cellophane cover that may be heat sealed to the outwardly projecting rim of the cup. The bottom of the cup is provided with a downwardly disposed projection that is adapted to be slip-fitted or snap-connected to a supporting, split, finger ring made of more permanent material since the ring is not considered to be disposable with the cup.

U.S. Pat. No. 2,970,379 (Hardgrove, 1961) discloses a sterilizable, vertically disposed and pivotally connected, two-compartment, finger supportable dental tray for holding plastic filling materials, dental cleaning compounds and medications wherein the upper compartment forms a closure for the lower compartment and the lower compartment is provided with a lateral rim that has a finger-engagable ring like member extending therefrom.

U.S. Pat. No. 4,717,057 (Porteous, 1988) discloses a disposable dental paste cup having an open mouth defined by an outwardly disposed lateral rim, a removable closure overlies the open mouth and extends beyond the rim, and a finger mount extends in a ring-like manner from the rim and terminates in an open end that passes through an aperture in the finger mount into alignment with the outer extension of the closure. The application of a vertical squeezing force to the finger mount permits the open end segment to bear against the outer extension of the closure and thereby effect displacement of the closure from the mouth of the cup.

SUMMARY OF THE INVENTION

An important object of this invention is to provide an economical and efficient method for configuring thermoplastic sheet into a dispensing cup, particularly, a dental dispensing cup having an integrated finger mount.

In accordance with this invention, there is provided a method for preparing a substantially fluid impervious, sealed, dental paste dispensing cup having an integrated finger mount, which comprises:

(a) forming a portion of a substantially fluid impervious, yieldable, plastic sheet into a cup having an open end and a closed end;

(b) adding dispensable, dental paste material to said cup through said open end;

(c) placing a sealable closure over the open end of said cup and marginally beyond the periphery of said open end to provide an overlap area that includes a pre-determined, outwardly disposed, lateral rim section;

(d) sealing said closure to the lateral rim section of said plastic sheet;

(e) excising said lateral rim section, with its subtending cup, from said plastic sheet in a configuration that includes an elongated handle portion extending outwardly from the periphery of said rim; and (f) shaping said elongated handle portion into the form of an elastically yieldable finger mount to provide a slide-resistant grip on a support finger.

The plastic sheet which can be used in the method of the invention advantageously comprises thermoplastic material such as polyethylene, polypropylene, polyvinyl chloride, ABS (acrylonitrile-butadine-styrene), acetal plastics, acrylic plastics, cellulosic plastics, fluoroplastics, nylons, polyphenyl oxide (PPO), polycarbonates, linear thermoplastic polyester, and the like.

The thermoplastic sheet is converted into a plurality of cup configurations by subjecting the sheet to the operations of a multi-cavity, thermoforming machine, commonly called a vacuum former, wherein the sheet is heated to a pliable, plastic state and forced by vacuum, or other technique against the contours of each cavity where, upon cooling, the plastic retains the shape and detail of the cavity. The various aspects of thermoforming, including: (a) sheet materials, (b) machines, (c) molds, (d) techniques of thermoforming, (e) thermoforming variables and (f) finishing, are extensively reviewed in the following reference: W. K. McConnell Jr., Thermoforming, *Modern Plastic Encyclopedia*, Vol 45, No. 14a, pp 776-792, McGraw Hill, 1968-1969.

Upon completion of the thermoforming step, the subtending cups of the plastic sheet are filled with a dispensable material such as dental paste. This step is advantageously carried out at a dispensing station provided with equipment for feeding into each cup a preselected quantity of dispensable material.

After the filling step is completed, a sealable closure is placed over the open end of each filled cup and marginally beyond the open end to provide an overlap area that includes a pre-determined, outwardly disposed, lateral rim section. Typically, the cups are disposed in the plastic sheet in linearly aligned rows and a sealable closure is configured and adapted to overlie each row. In one embodiment, the sealable closure has an inner face comprising heat sealable material and the closure is heat sealed to the plastic sheet. In an alternative embodiment, the sealable closure has an inner face comprising pressure sensitive adhesive and the closure is adhesively secured to the plastic sheet.

The sealing of the closure to the plastic sheet is followed by a die-cutting step wherein each lateral rim section, with its subtending cup, is excised from the plastic sheet in a configuration that includes an elongated handle portion extending outwardly from the rim. The closure sealing step and the die-cutting step can be carried out at a station suitably equipped for this purpose.

The cup is completed by shaping the elongated handle portion into the form of a finger mount. This shaping step can be advantageously effected by thermoforming technique wherein the elongated handle is heated to a pliable, plastic state and the outer end of the handle is rotated inwardly in a clockwise manner to thereby bring the outer end into proximate relationship with the rim of the cup. In a preferred embodiment, the apogee of the resulting finger mount is substantially in alignment with the lateral rim of the cup.

In a further embodiment of the invention, the configuration produced by excising the lateral rim section from the plastic sheet also includes a pull-open tab extending outwardly from the periphery of the lateral rim section wherein the underlying plastic sheet of the closure laminate is provided with a transverse cut to facilitate removal of the closure at the time of use.

DETAILED DESCRIPTION

Figure 1:
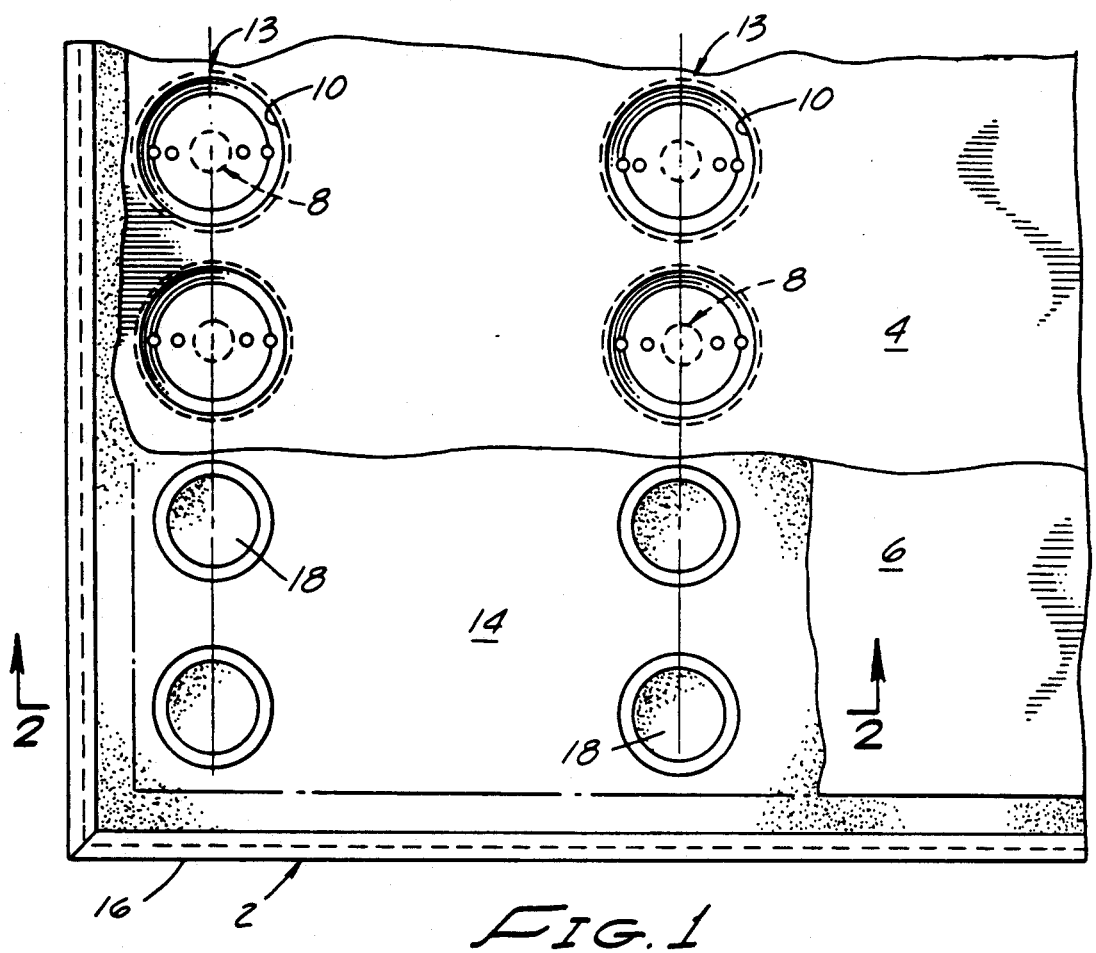
FIG. 1 is a partial, schematic, top plan view of a thermoplastic sheet overlying the mold cavities of a thermoforming machine.
Figure 2:
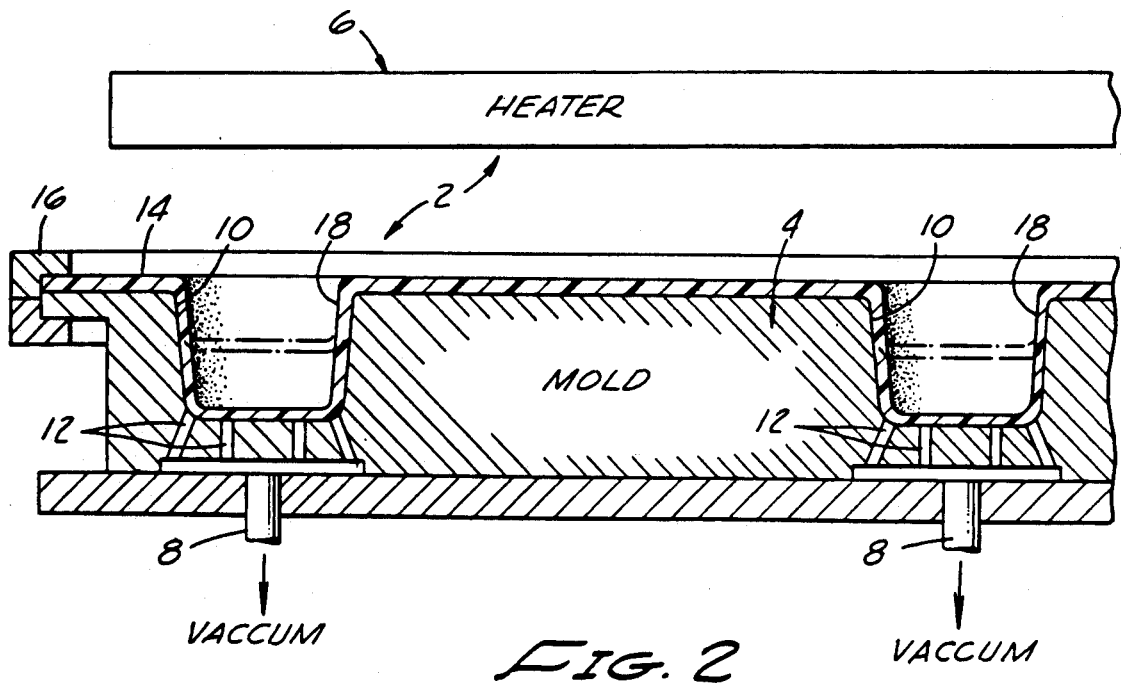
FIG. 2 is a schematic, side elevational view taken along line 2—2 of FIG. 1 showing the heater, mold cavities and vacuum forming system wherein a thermoplastic sheet portion has been drawn into each mold cavity to thereby acquire a cup-like configuration.

Referring now to the drawings and, in particular, to FIGS. 1 and 2, there is shown, in schematic form, a thermoforming machine 2 that includes a mold 4, a superimposed heating unit 6, and a vacuum exhaust system 8. The mold is provided with a plurality of cup-configured cavities 10 having exhaust conduits 12 which are integral with the exhaust system. The cavities are advantageously disposed in linearly aligned rows 13 so as to permit the formation of cups having elongated handle portions, as hereinafter described.

A thermoplastic sheet 14 comprising polyethylene or polypropylene or other suitable thermoplastic material is placed over the mold 4 and secured thereto by appropriate clamping mechanism 16. The application of heat to the thermoplastic sheet 14 and the vacuum evacuation of the mold cavities softens the sheet and forces the softened sheet against the contours of each cavity where, upon cooling, the plastic retains the cup configuration 18 of the cavity 10.

Figure 3:
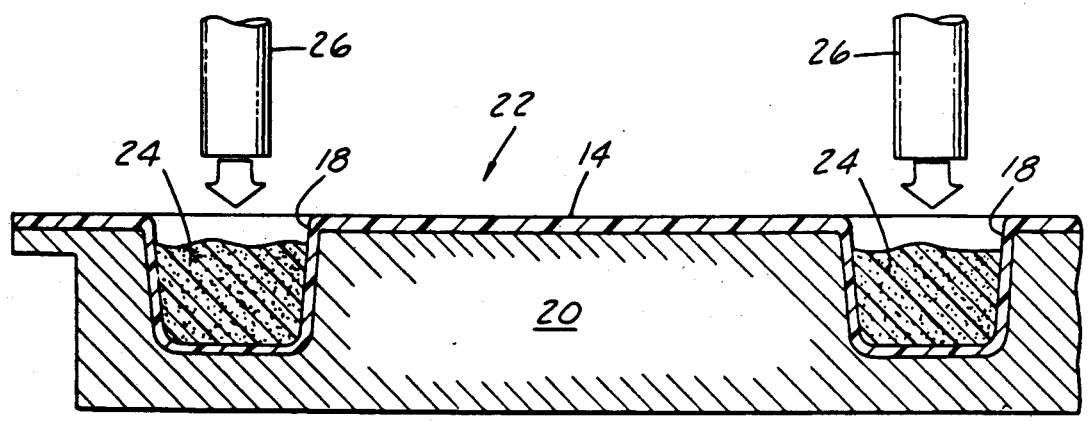
FIG. 3 is a schematic, side elevational view of a dispensing station showing a multi-cup, plastic sheet in a support structure, with the cups positioned to receive, and receiving, dispensable material such as dental paste from filling spouts.

The plastic sheet 14 with its subtending cups 18 is transferred to a support structure 20 at a dispensing station 22 where a dispensable material such as dental paste 24 is metered into the cups through filling spouts 26, as shown in FIG. 3.

Figure 4:
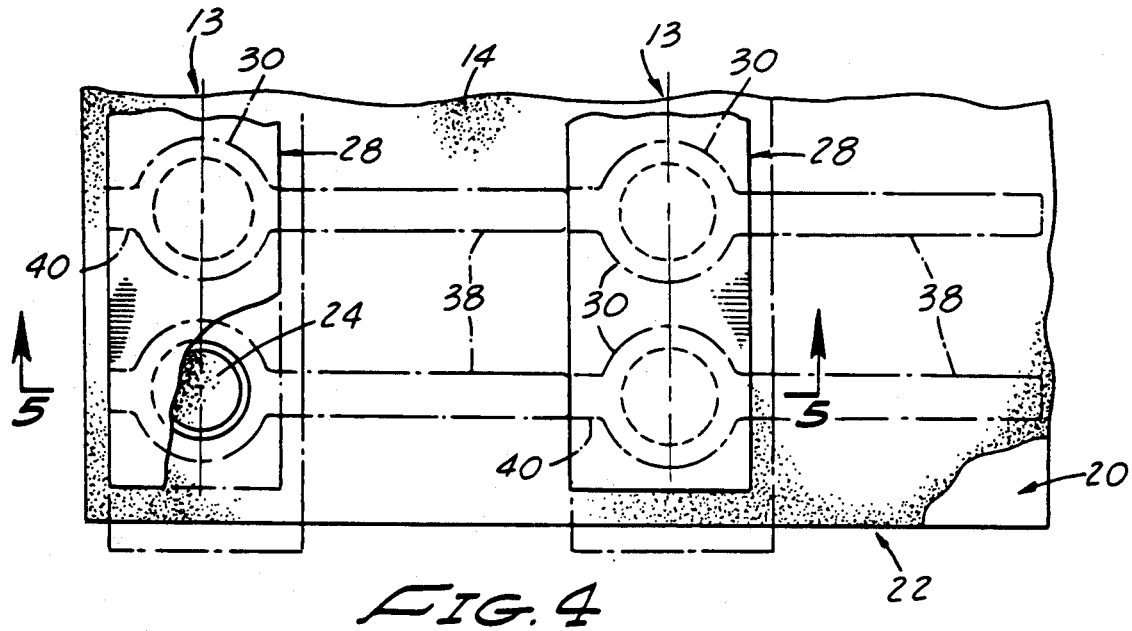
FIG. 4 is a partial, schematic, top plan view of a heat sealing and die-cutting station showing first and second, heat sealable, closure strips overlying first and second rows, respectively, of cups filled with dispensable material, with the configuration to be excised from the plastic sheet being shown in phantom outline.
Figure 5:
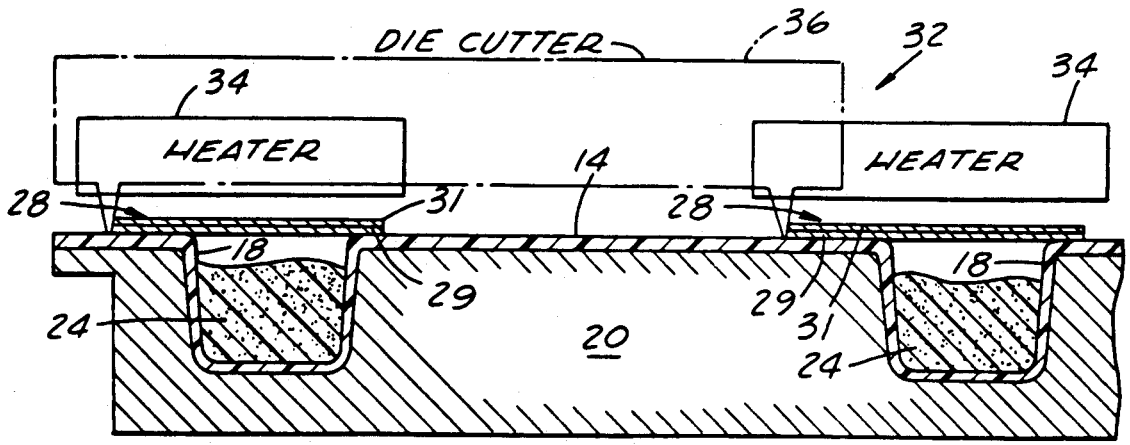
FIG. 5 is a schematic, side elevational view taken along line 5—5 of FIG. 4 showing a heating unit for heat sealing the closure to the plastic sheet and showing a die-cutter for excising the cup from the plastic sheet in a configuration that includes a rim having an outwardly extending handle portion and an outwardly extending pull-open tab.

A sealable closure strip 28 is placed over each row 13 of the filled cups in the plastic sheet and extends marginally beyond the open end of each cup to provide an overlap area that includes a pre-determined, outwardly disposed lateral rim section 30, as shown in FIG. 4. The closure strip has an inner face 29 and an outer face 31, with the inner face comprising heat sealable material such as polyethylene. The outer face may advantageously be aluminum foil or other suitable material such as cellophane, paper, plastic, metalized plastic, and the like.

Figure 6:
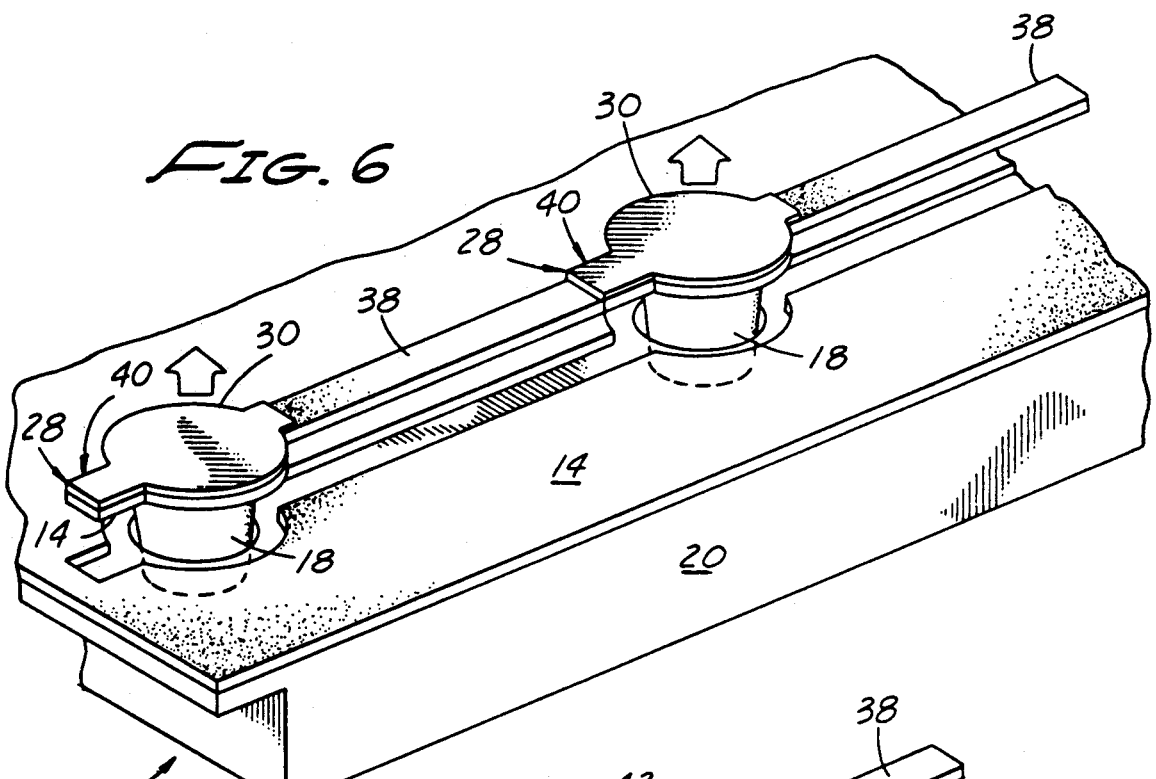
FIG. 6 is a semi-exploded, perspective view showing a pair of excised cups as removed from the plastic sheet.
Figure 7:
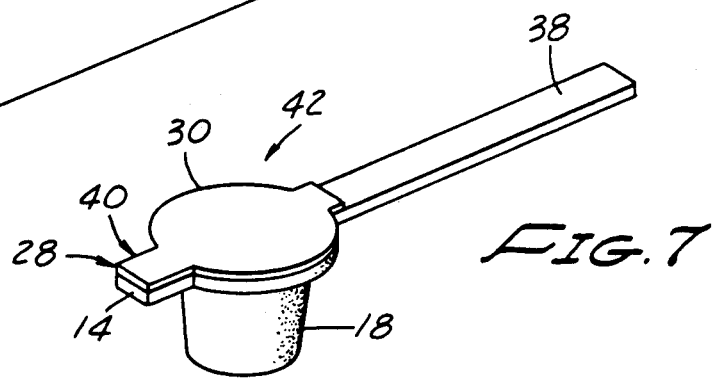
FIG. 7 is a perspective view of the filled and sealed, dispensing cup, as removed and separated from the thermoplastic sheet.

At a heat sealing and die-cutting station 32 equipped with a heater 34 and die cutter 36, the closure strip 28 is heat sealed to the plastic sheet 14. This heat sealing step is followed by a die-cutting step wherein each lateral rim section 30, with its subtending cup 18, is excised from the plastic sheet in a configuration that includes an elongated handle portion 38 and a pull tab 40, as shown in FIGS. 4, 6 and 7.

Figure 8:
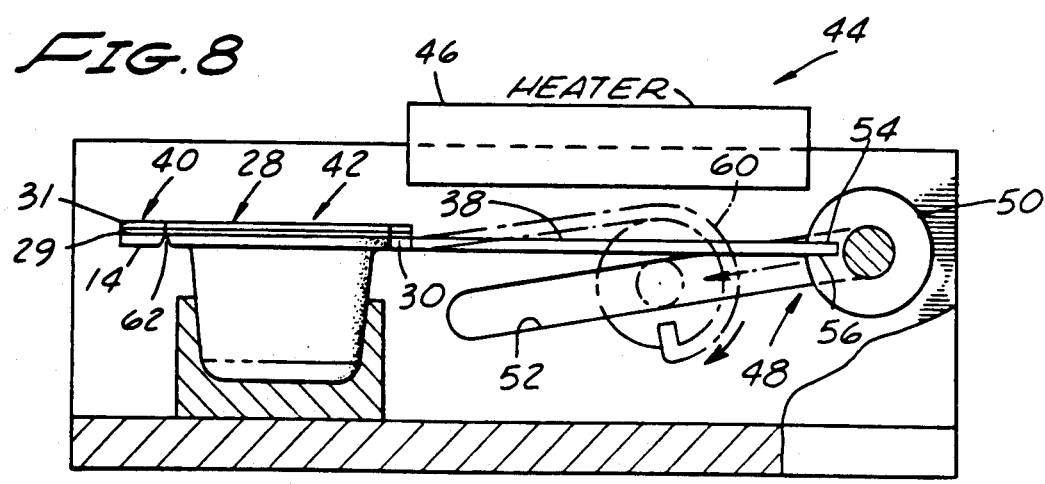
FIGS. 8 and 9 are schematic, side elevational views showing the formation of a finger mount by heating the elongated handle portion and rotating the outer end thereof in a clockwise manner so as to place the outer end in proximity with the rim of the cup.
Figure 9:
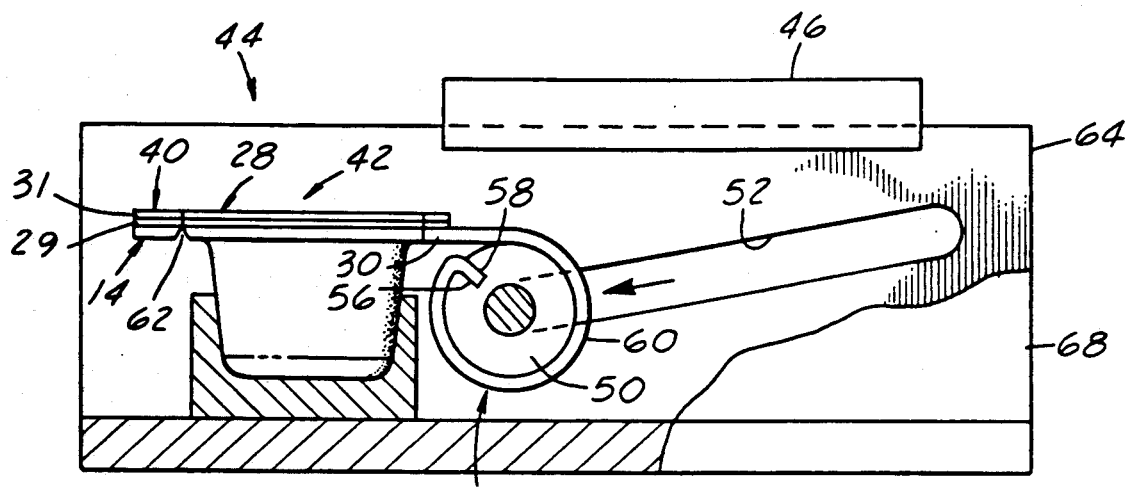
Figure 10:
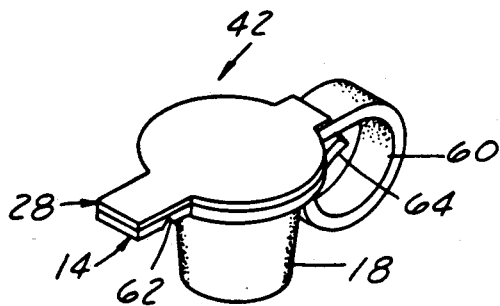
FIG. 10 is a perspective view of the disposable, finger mountable, filled and sealed dispensing cup and shows a transverse cut in the underlying plastic sheet of the pull-open tab to facilitate removal of the closure at the time of use.
Figure 11:
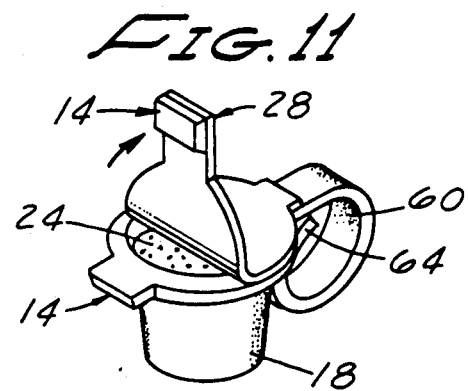
FIG. 11 is a perspective view of the filled and sealed dispensing cup and shows the closure partially removed from the rim of the cup.

The excised cup 42 is transferred to a forming station 44 equipped with a heater 46 and a finger mount forming assembly 48 that includes a rotatable slotted disk 50 and an inclined support guide 52, as shown in FIGS. 8 and 9. At the forming station, the outer end 54 of the cup elongated handle portion 38 is inserted into the slot 56 of the disk 50. The elongated handled portion 38 is heated and then rotated in a clockwise manner by the disk while simultaneously moving the disk toward the cup along a declining angle whereby the outer end of the elongated handle is brought into proximity with the rim 30 of the cup to thereby form the finger mount 60. The inwardly directed, angular end 58 of the finger mount 60 can be heat softened and rotated into an arcuate configuration 64, as shown in FIG. 10 or the outer end 58 can be removed by trimming. In a further embodiment, the underlying plastic sheet 14 of the laminated pull tab 40 is advantageously provided with a transverse cut 62 so as to facilitate removal of the closure strip at the time of use.

Figure 12:
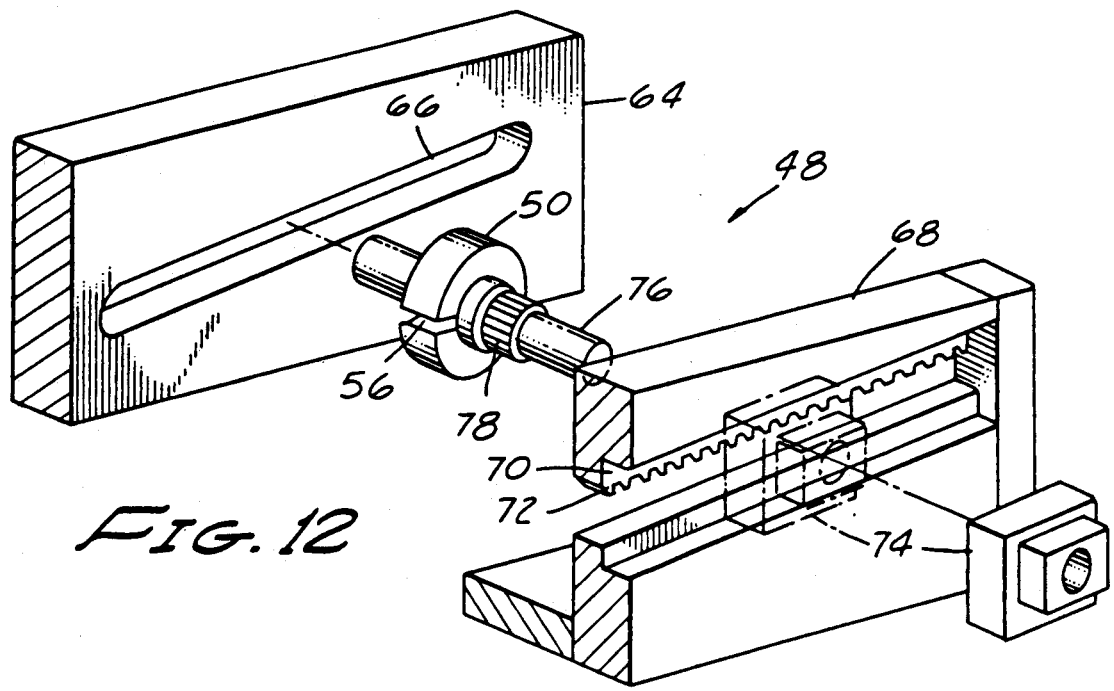
FIG. 12 is a schematic, perspective view of a rack and gear assembly that includes a slotted forming disk for receiving the outer end of the elongated handle and rotating the handle to form the finger mount.

An illustrative forming assembly for transforming the elongated handle portion 38 into an annular finger mount 60 is shown in FIG. 12. The assembly includes (a) a first guide plate 64 having a sloping linear slot 66, (b) a second guide plate 68 in spaced relationship to the first guide plate and having a sloping, recessed, journal block support 70 with an upper row of linear gear teeth 72, (c) a slidable journal block 74 disposed in the recess 70, and (d) a shaft 76 equipped with a slotted forming disk 50 and a spur gear 78 for engaging the linear gear teeth.

In contrast to U.S. Pat. No. 4,571,924 (Bahrani, 1986) which discloses porous flow-through tea bags that may incorporate a relatively rigid handle or stirrer, the invention herein is directed to a method for preparing a substantially fluid impervious, sealed, dental paste dispensing cup having an integrated holder in the form of an elastically yieldable finger mount to provide a slide-resistant grip on a support finger.

While in the foregoing description and accompanying drawings, there has been shown and described the preferred embodiment of this invention, it will be understood, of course, that minor changes may be made in the details of construction as well as in the combination and arrangement of parts without departing from the spirit and scope of the invention as claimed.

That which is claimed is:

1. A method for preparing a substantially fluid impervious, sealed, dental paste dispensing cup having an integrated finger mount, which comprises:
   forming a portion of a substantially fluid impervious, yieldable, plastic sheet into a cup having an open end and a closed end;
   adding dispensable, dental paste material to said cup through said open end;
   placing a sealable closure over the open end of said cup and marginally beyond the periphery of said open end to provide an overlap area that includes a pre-determined, outwardly disposed, lateral rim section;
   sealing said closure to the lateral rim section of said plastic sheet;
   excising said lateral rim section, with its subtending cup, from said plastic sheet in a configuration that includes an elongated handle portion extending outwardly from the periphery of said rim; and
   shaping said elongated handle portion into the form of an elastically yieldable finger mount to provide a slide-resistant grip on a support finger.

2. The method of claim 1 wherein said plastic sheet comprises thermoplastic material and said cup is configured by thermoforming said thermoplastic sheets.

3. The method of claim 1 wherein said sealable closure has an inner face comprising heat sealable material and said closure is heat sealed to said plastic sheet.

4. The method of claim 1 wherein said sealable closure has an inner face comprising pressure sensitive adhesive and said closure is adhesively sealed to said plastic sheet.

5. The method of claim 2 wherein said elongated handle portion is heated and annularly rotated to bring the outer end of said handle portion into proximate relationship with the lateral rim of said cup to thereby form said finger mount.

6. The method of claim 5 wherein said handle portion is rotated towards the closed end of the cup and the apogee of the resulting finger mount is substantially in alignment with said lateral rim.

7. The method of claim 1 wherein the configuration produced by excising said lateral rim section from said plastic sheet also includes a pull-open tab extending outwardly from the periphery of the lateral rim section.

8. The method of claim 7 which includes the step of making a cut in the underside of said tab to facilitate the removal of the closure at the time of use.

* * * * *